(12) United States Patent
O'Brien et al.

(10) Patent No.: US 9,333,154 B2
(45) Date of Patent: May 10, 2016

(54) DUAL COMPONENT ORAL COMPOSITION FOR ENHANCING REMINERALIZATION OF TEETH

(71) Applicants: Thomas Ray O'Brien, Houston, TX (US); Kimberlee U. Martin, Bellaire, TX (US)

(72) Inventors: Thomas Ray O'Brien, Houston, TX (US); Kimberlee U. Martin, Bellaire, TX (US)

(73) Assignee: M & O Solutions, LLC, Houston, TX (US)

( * ) Notice: Subject to any disclaimer, the term of this patent is extended or adjusted under 35 U.S.C. 154(b) by 0 days.

(21) Appl. No.: 14/340,563

(22) Filed: Jul. 25, 2014

(65) Prior Publication Data

US 2016/0030306 A1    Feb. 4, 2016

Related U.S. Application Data

(63) Continuation-in-part of application No. 14/150,551, filed on Jan. 8, 2014, now abandoned, which is a continuation of application No. 13/349,110, filed on Jan. 12, 2012, now abandoned.

(51) Int. Cl.
| | | |
|---|---|---|
| *A61Q 11/00* | (2006.01) |
| *A61K 8/21* | (2006.01) |
| *A61K 8/22* | (2006.01) |
| *A61K 8/24* | (2006.01) |
| *A61K 33/06* | (2006.01) |
| *A61K 8/19* | (2006.01) |
| *A61K 8/04* | (2006.01) |

(52) U.S. Cl.
CPC . *A61K 8/19* (2013.01); *A61K 8/042* (2013.01); *A61Q 11/00* (2013.01)

(58) Field of Classification Search
USPC ................. 424/49, 401, 52, 57; 433/215, 216
See application file for complete search history.

(56) References Cited

U.S. PATENT DOCUMENTS

| | | | |
|---|---|---|---|
| 4,788,052 A | 11/1988 | Ng et al. | |
| 5,085,853 A | 2/1992 | Williams et al. | |
| 5,597,554 A | 1/1997 | Wagner | |
| 5,820,852 A * | 10/1998 | Burgess et al. | 424/52 |
| 5,902,568 A | 5/1999 | Ryles et al. | |
| 5,980,869 A * | 11/1999 | Sanker et al. | 424/58 |
| 6,086,856 A | 7/2000 | Saferstein et al. | |
| 2013/0183253 A1 | 7/2013 | Martin et al. | |

* cited by examiner

*Primary Examiner* — Lezah Roberts
(74) *Attorney, Agent, or Firm* — Ramey & Schwaller, LLP

(57) ABSTRACT

An dual oral composition is provided having a first peroxide-containing component and a second bicarbonate-containing component having exceptional anti-plaque and antibacterial action with re-mineralization properties.

4 Claims, 7 Drawing Sheets

| | | |
|---|---|---|
| Hydrogen Peroxide | 75% (75mg/ml) | Cleansing Agent |
| Saccharin Sodium | 0.1% (1mg/ml) | Sweetener |
| Polysorbate 20 | 0.2% (2mg/ml) | Emulsifier |
| Sorbitol Solution 70% | 10.5% (10.5mg/ml) | Humectant |
| Spearmint Oil | 0.303% (3.03mg/ml) | Flavoring |
| Poloxamer 407 25% | 25% (250mg/ml) | Surfacent |
| Peppermint Oil | 0.303% (3.03mg/ml) | Sweetener |

Figure 4

| | | |
|---|---|---|
| Sodium Flouride | 1.1% (11mg/ml) | Mineralization Agent |
| Sodium Bicarbonate | 25% (250 mg/ml) | Baking Soda |
| Calcium Carbonate | 25% (250mg/ml) | Mineralization Agent |
| Sodium Chloride | 3% (30mg/ml) | Salt |
| Polysorbate 20 | 27.8% (278mg/ml) | Emulsifier |
| Xylitol | .1% (10mg/ml) | Stop Grinding Batin |
| Citric Acid USP | 0.2% (2mg/ml) | Flavoring |
| Flavor, Artificial, Marshmallow | 1.5% (15 mg/ml) | Flavoring |
| Stevioside 15% Liquid Extract | 3.5% (35mg/ml) | Sweetner |
| Spearmint Powder | 2% (2g/ml) | Flavoring |

Figure 5

DUAL COMPONENT ORAL COMPOSITION FOR ENHANCING REMINERALIZATION OF TEETH

This patent claims the benefit of application Ser. No. 14/150,551

BACKGROUND OF THE INVENTION

1. Field of the Invention

The present invention relates to a dual composition dentifrice, more particularly to a composition of dentifrice that achieves significant effects for preventing dental caries and periodontal disease.

2. The Related Art

Tooth decay, or dental caries, is an infectious disease, the key feature of which is an increase within dental plaque of aerobic bacteria such as *Streptococcus Mutans* and *Lactobacillus* coming in contact with sugar. Tooth decay is an infection which results in the demineralization of the hard tissues. If left untreated, the disease causes increased hypersensitivity, pain and ultimately death of the tooth as the infection reaches the softer, interior part of the tooth called the pulp. Demineralization occurs when carbohydrates, especially sugar, is eaten, producing organic acids and the acids come in contact with the tooth structure. When enough acid is produced so that the pH goes below 5.5, the process begins. Teeth are porous allowing acidic fluids to come in contact not only with enamel, which is above the gums, but also the cementum, which is the tooth surface normally below the gum line. When demineralization occurs, those pores become larger, forming cavities within the tooth structure. Remineralization is the process in which minerals are returned to the molecular structure of the tooth itself.

Periodontal disease is also an infectious disease that attacks the supporting structures that surround the teeth, namely bone, connective and gum tissue. The bacteria responsible for periodontal disease are anaerobic, and they thrive in an acidic, oxygen-free environment. In the presence of sugar, the anaerobic bacteria use that sugar and excrete a strong acid as a by-product of the metabolism of the sugar. In response to the toxic nature of the acid, the gum tissue becomes very inflamed and begins to pull away from the side of the tooth and root surface. As the gums pull away from the tooth and root surfaces, spaces are formed, called "pockets". Bacterial toxins and the body's natural response to infection start to break down the bone and connective tissue that hold teeth in place. If not treated, the bones, tissue and gums that support the teeth are destroyed, which can eventually lead to teeth becoming loose and having to be removed.

The present invention provides for a new composition that enhances the remineralization process inhibiting tooth decay, and it neutralizes and oxygenates the periodontal environment eliminating the furtherance of the periodontal disease process.

SUMMARY

An oral composition is provided including a bicarbonate and peroxide component. Accordingly, it is an object of the present invention to provide a dual component. Composition that enhances the remineralization process of tooth enamel and cementum, Wherein tooth decay is prevented, and it also provides a neutral, oxygenated environment so that periodontal disease is also prevented. These and other objects of the present invention will become more readily apparent through consideration of the following summary and detailed description.

BRIEF DESCRIPTION OF DRAWINGS

FIG. 4 illustrates the formulation of the gel component of the composition;
FIG. 5 shows the formulation of the paste component of the composition.

DETAILED DESCRIPTIONS

The present invention comprises a dual component oral composition for the prevention of tooth decay and periodontal disease. The dual composition comprises a first cleansing agent base gel and a second sodium bicarbonate paste. The dual composition is used in conjunction with one another in a 1:1 ratio. Beyond the first essential ingredient of hydrogen peroxide of the first component there will also be included a pharmaceutical acceptable carries including surfactant, humectants, thickening agent and sweeteners. The bicarbonate component contains xylitol and prescription strength neutral sodium fluoride. The xylitol is a non-fermentable sugar alcohol which has been shown to not only reduce dental decay significantly, but also has re-mineralization capability in combination with other ingredients in the bicarbonate component. Xylitol has an alkaline makeup which inhibits anaerobic bacteria. The neutral sodium fluoride also re-mineralizes the tooth surface and prevents decay. The peroxide component provides oxygen to be released when introduced to the bicarbonate component and water is introduced.

The oxygen released inhibits the anaerobic bacteria that must live in an oxygen-free environment. Additionally, the bicarbonate component is basic in nature and neutralizes the harmful acidic environment, and once again the anaerobic bacteria cannot survive in a non-acidic environment. The salt or sodium chloride within the component reduces the inflammation of the gum tissue as well as inhibits the anaerobic bacteria during osmosis. These three properties provided by the formulation of the present invention oxygenation, neutralization and osmosis reverse the environment conducive to periodontal disease.

The present invention comprises a dual component oral composition for the prevention of tooth decay. The dual composition comprises a first cleansing agent base gel and a second sodium bicarbonate paste. The dual composition is used in conjunction with one another in a 1:1 ratio.

The cleansing agent of the first component is a peroxide compound, preferably hydrogen peroxide. Beyond the first essential ingredient of hydrogen peroxide of the first component there will also be included pharmaceutical acceptable carries including surfactant, humectants, thickening agent and sweeteners.

Peroxide Gel Cleansing Agent

Figure 3:
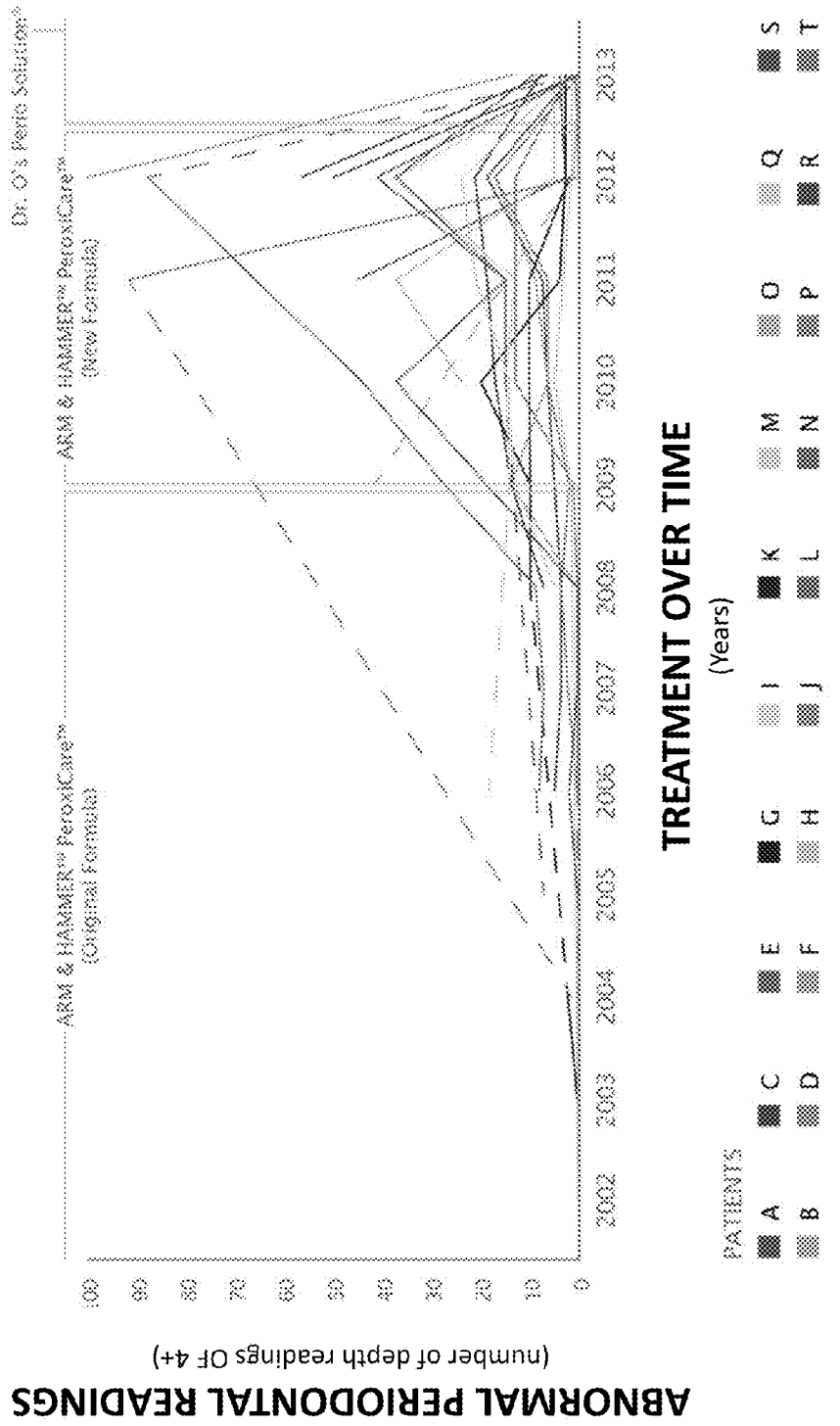
FIG. 3 illustrates the results of several patients that used the formulation.

A first essential component or cleansing agent of compositions according to the present invention is that of a peroxide compound. In this composition as shown in FIG. 3, hydrogen peroxide of approximately 7.5% by weight.

Polysorbate 20 NF is the surfactant which can be incorporated to provide foaming properties. Sorbitol Solution USP 70% by weight is the humectant or wetting agent which prevents the water in the composition from evaporating.

Sweetness and flavoring agents can be used to ensure good taste during tooth brushing or for a freshening aftertaste after toothbrushing. In this gel component, Saccharin Sodium USP Dihydrate is the sweetener and Methyl Salicylate NF and Peppermint Oil are the flavorings. Poloxamer 407 25% gel is the thickening agent. Hydrogen peroxide is the preferred essential cleansing agent which ranges about 7.5% by weight.

Method of Preparation of Hydrogen Peroxide Gel

In an appropriate container mix saccharin sodium and polysorbate 20 in sorbitol Solution until completely dissolved. Then add flavoring to the above mixture. Add hydrogen peroxide to the mixture and place in an ice bath until uniform mixture is formed. Transfer mixture to containers and let stand at room temperature.

Method of Preparation of the Potassium Sorbate Gel

Mix Potassium Sorbate and Poloxamer 407 25% gel in a container and bring to final volume with cold refrigerated purified water. Refrigerate resultant mixture when all granules of potassium sorbate are mixed thoroughly and it takes up to 12 to 24 hours within the refrigerator before the mixture becomes a clear solution. Once the mixture becomes a clear solution, the gel will solidify at room temperature.

Second Component

The second oral composition comprises the following essential compounds: Sodium Bicarbonate, Xylitol, and a re-mineralization agent including Calcium Carbonate or Calcium Phosphate or, Dibasic USP Anhydrous of equivalent percentage of weight. Along with these compounds, the composition will also include sodium chloride (salt), flavorings, and a thickening agent. Polysorbate 20 NF is the thickening agent and the flavorings include Spearmint oil or peppermint oil, citric acid USP monohydrate powder, marshmallow, stevioside 15% liquid extract, and spearmint powder. Sweetener is Xylitol in this component.

A second essential component of compositions is that of sodium bicarbonate with a preferred weight of 25%.

A third essential component of compositions according to the present invention is xylitol which is 0.1% by weight. Xylitol is a non-fermentable sugar alcohol which has dental health benefits in caries prevention. It has a plaque-reducing effect that attracts and starves harmful micro-organisms, allowing the mouth to re-mineralize damaged teeth with less interruption. Xylitol specifically inhibits the streptococci mutans group. It inhibits streptococci mutans in the presence of other sugars with the exception of fructose. Saliva containing xylitol is more alkaline than saliva which contains other sugar products. When saliva is alkaline, the calcium and phosphate salts in saliva start to precipitate into those parts of enamel where they are lacking thereby allowing the tooth to effectively remineralize.

A fourth essential component of compositions is sodium fluoride that is 1.1% by weight. The humectant sugar alcohol solution is optimally 10.5% by weight. This is a remineralization agent.

A fifth essential compound of the present invention is calcium carbonate which is preferably 25% by weight. This is a re-mineralization agent. An alternative re-mineralization agent is calcium phosphate, Dibasic USP Anhydrous.

The oral composition of the present invention for the hydrogen peroxide gel can be prepared in the preferred embodiment as described below in FIG. 4.

The oral composition of the present invention for the sodium bicarbonate paste can be prepared in the preferred embodiment as described below in FIG. 5.

Method of Preparation of Sodium Bicarbonate Paste

At room temperature, in a container, with a mortar and pestle, triturate Sodium Bicarbonate, Sodium Chloride and Calcium Carbonate together. Then wet with enough glycerin until a thick smooth paste is formed. Then add flavorings and levigate thoroughly.

Figure 1:
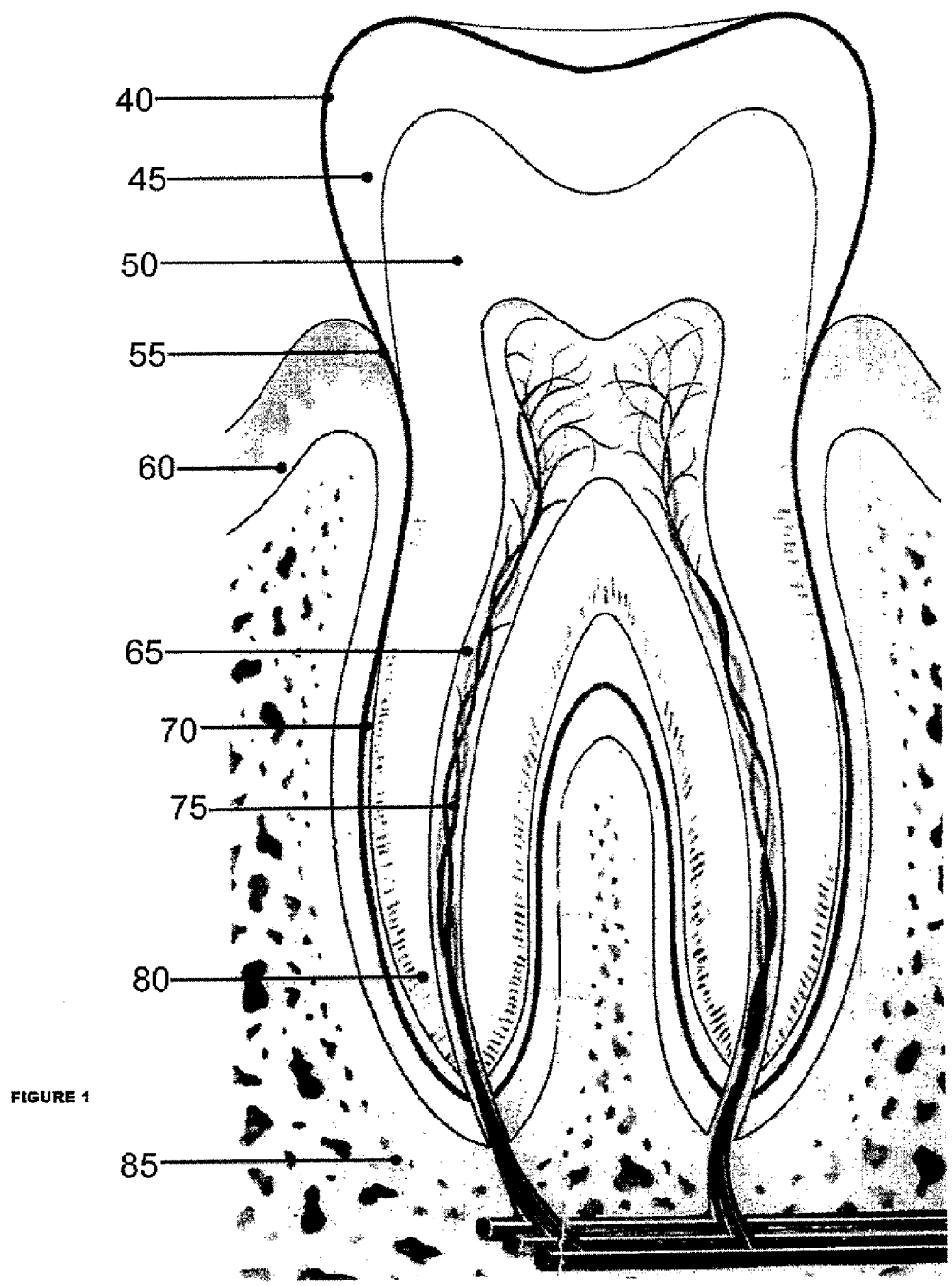
FIG. 1 illustrates a normal tooth.

FIG. 1 depicts a cross-sectional view of a normal tooth. As shown, the gums (60) are attached by the gingival fibers to the surface of the enamel (45) and the space created by the side of the tooth and the gum tissue is the gingival crevice (55). Enamel (45) is a hard white substance covering the crown of the tooth. The pulp (65) is the central part of the tooth that includes the living blood vessels and sensory nerves (75) that extend into the root (80) of the tooth near the bone (85) and out into the surrounding bone and enables sensation within the tooth. The gingiva or the gum tissue (60) is the tissue that lies over the bone (85) around and between the teeth. Cementum (70) is the calcified substance covering the root (80) of the tooth. Dentin (50) is the calcified substance lying below the enamel (45) covering the pulp (65).

Figure 2:
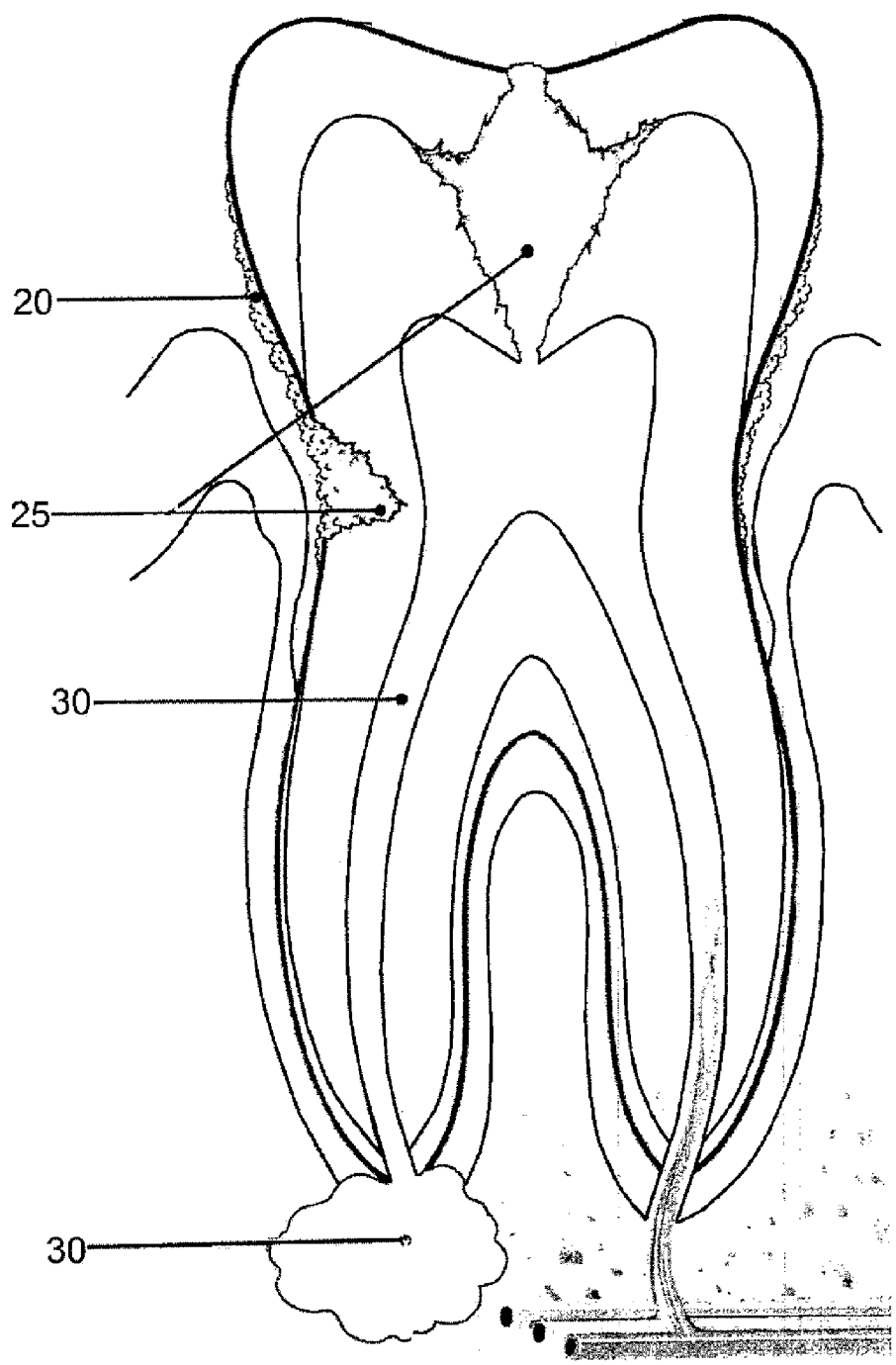
FIG. 2 illustrates a diseased tooth.

FIG. 2 depicts a cross-sectional drawing of an illustration of a diseased tooth. Depicted in FIG. 2 the gingival fibers have detached from the surface of the enamel (45) of the diseased tooth forming gingival crevice (55). Plaque is present that has formed at the gumline and below the gumline. Caries, or decay, has formed within the enamel (45) of the tooth. An infection or abscess (30) is shown at the tip of the root and infection is shown within the root of the tooth.

Figure 6:
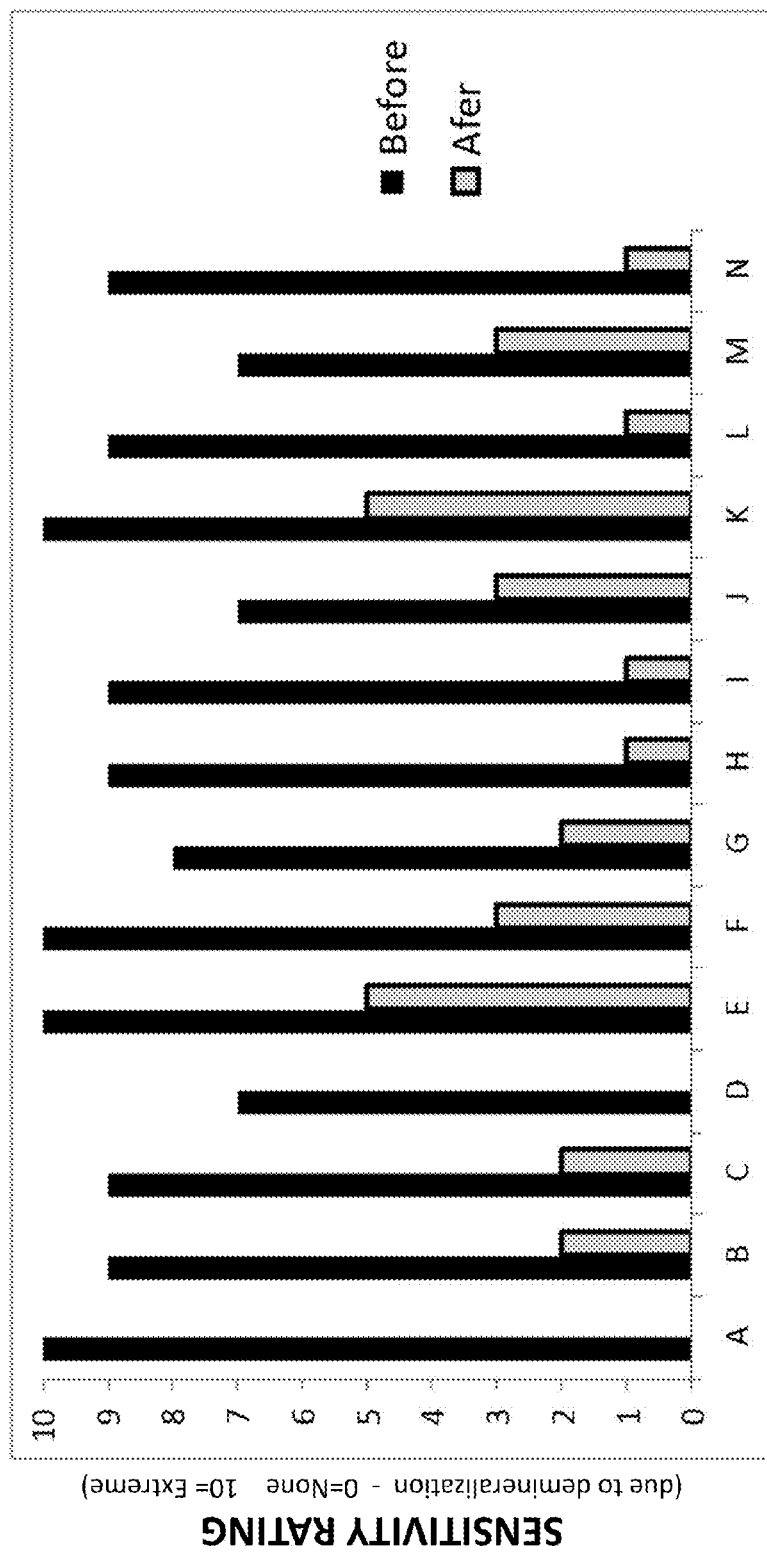
FIG. 6 illustrates the hypersensitivity level of several patients that used the formulation.
Figure 7:
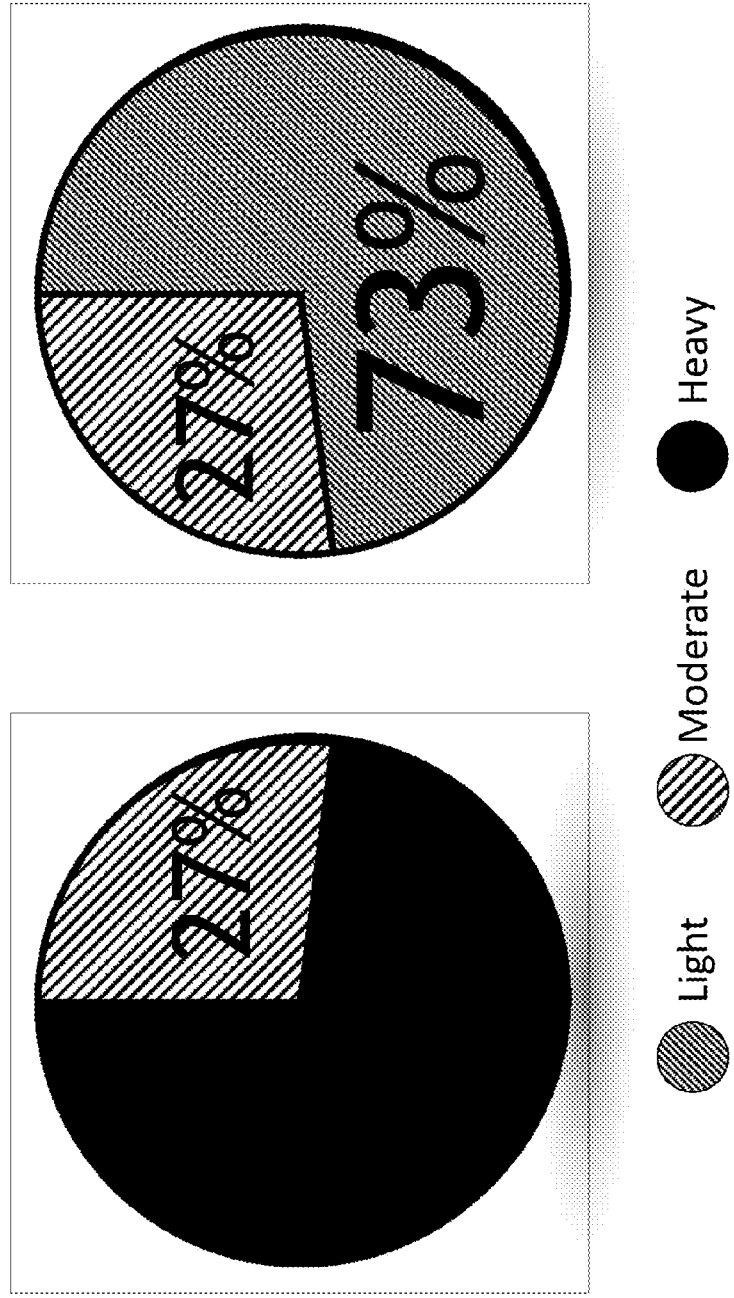
FIG. 7 illustrates the tartar buildup of the patients.

The applicant used the formulation in FIGS. 4 and 5 on various patients with the results shown in FIGS. 3, 6 and 7. Prior to using the formulation, several of the patients had diseased gums at various stages. After using the formulation, their gums, or periodontal condition, improved significantly and showed significant signs of re-mineralization. The level of detachment of the gums showed significant signs of re-attaching, improving to within normal limits with a gingival crevice (55) of 3 mm or less as shown in FIG. 3 and less tarter buildup as shown in FIG. 7. FIG. 6 show the decrease in hypersensitivity of the patients that used the formulation in FIGS. 4 and 5.

What is claimed is:

1. A dual component oral composition dentifrice for repairing damaged teeth that are hypersensitive or with periodontal pocketing comprising:
    a gel component comprising:
        a hydrogen peroxide compound present in an amount of approximately 7.5% by weight of the gel component;
        a sorbitol component in an amount of approximately 10.5% by weight of the gel component; and
    a paste component comprising:
        sodium bicarbonate in an amount of approximately 25% by weight of the paste component;
        a sodium fluoride component in an amount of approximately 1.1% by weight of the paste component;
        a xylitol anti-plaque forming agent in an amount of approximately 0.1% by weight of the paste component; and
        a re-mineralization agent selected from the group consisting of calcium carbonate and calcium phosphate that works in combination with the anti-plaque forming agent to re-mineralize damaged teeth; and
        wherein hypersensitivity is reduced or periodontal pocketing is reduced.

2. The oral composition of claim 1 wherein the gel component further comprises polysorbate 20 in an amount of 0.2% by weight of the gel component.

3. The oral composition of claim 1 wherein the gel component further comprises sweeteners.

4. The oral composition of claim 1 wherein the gel component further comprises flavoring.

\* \* \* \* \*